US012088405B2

(12) United States Patent
Aasen et al.

(10) Patent No.: US 12,088,405 B2
(45) Date of Patent: Sep. 10, 2024

(54) SYSTEMS AND METHODS FOR CONTROLLING HOSPITALITY DISTRIBUTION NETWORKS

(71) Applicant: SONIFI Solutions, Inc., Sioux Falls, SD (US)

(72) Inventors: Eric Aasen, Sioux Falls, SD (US); Joshua H. Pulford, Sioux Falls, SD (US); Leon P. Stoel, Sioux Falls, SD (US)

(73) Assignee: SONIFI SOLUTIONS, INC., Sioux Falls, SD (US)

(*) Notice: Subject to any disclaimer, the term of this patent is extended or adjusted under 35 U.S.C. 154(b) by 334 days.

(21) Appl. No.: 17/486,346

(22) Filed: Sep. 27, 2021

(65) Prior Publication Data
US 2022/0014290 A1  Jan. 13, 2022

Related U.S. Application Data

(63) Continuation of application No. 16/664,604, filed on Oct. 25, 2019, now Pat. No. 11,159,259.
(Continued)

(51) Int. Cl.
H04W 4/06      (2009.01)
H04H 20/63     (2008.01)
(Continued)

(52) U.S. Cl.
CPC ............ H04H 20/63 (2013.01); H04H 60/29 (2013.01); H04W 4/06 (2013.01); G16H 40/67 (2018.01);
(Continued)

(58) Field of Classification Search
None
See application file for complete search history.

(56) References Cited

U.S. PATENT DOCUMENTS 4,516,070 A  *  5/1985  Brown ..................... H04M 3/30
                                                324/130
5,917,815 A  *  6/1999  Byers ................. H04Q 11/0478
                                                370/395.51
(Continued)

FOREIGN PATENT DOCUMENTS

EP           766215 B1  *  6/2002   ............. G01S 13/74
WO      WO-0119005 A1  *  3/2001   ............. H04J 3/0644

OTHER PUBLICATIONS

Holla et al. "Advanced Monitoring System for Digital Cable Distribution Network," IEEE, 2017 WiSPNET 2017 Conference, pp. 1621-1623.
(Continued)

Primary Examiner — Idowu O Osifade
(74) Attorney, Agent, or Firm — Sheridan Ross P.C.

(57) ABSTRACT

A system includes a host device to provide a content signal, an end device to receive the content signal, and a branch of amplifiers connected between the host device and the end device to carry the content signal from the host device to the end device. The host device may receive a first signal from the branch of amplifiers connected to the end device, and extract, from the first signal, first characteristics of the content signal measured at one or more points in the branch of amplifiers. The host device may compare the first characteristics of the content signal to second characteristics. The host device may determine, based on the comparison, adjustments for one or more settings of a first amplifier of the amplifiers, and send a second signal to the branch of amplifiers to communicate the adjustments for the one or more settings to the first amplifier.

20 Claims, 7 Drawing Sheets

Related U.S. Application Data

(60) Provisional application No. 62/751,310, filed on Oct. 26, 2018.

(51) Int. Cl.
  *H04H 60/29* (2008.01)
  *G16H 40/67* (2018.01)
  *H04N 21/214* (2011.01)
  *H04N 21/24* (2011.01)

(52) U.S. Cl.
  CPC ..... *H04N 21/2143* (2013.01); *H04N 21/2402* (2013.01)

(56) References Cited

U.S. PATENT DOCUMENTS

| | | | |
|---|---|---|---|
| 9,701,236 | B2 * | 7/2017 | Thomsen ................ F03D 13/40 |
| 11,159,259 | B2 | 10/2021 | Aasen et al. |
| 2003/0149991 | A1 | 8/2003 | Reidhead et al. |
| 2005/0286436 | A1 | 12/2005 | Flask |
| 2008/0313694 | A1 | 12/2008 | Kudo et al. |
| 2009/0007210 | A1 | 1/2009 | Nishide et al. |
| 2014/0022943 | A1 | 1/2014 | Ling et al. |
| 2015/0029869 | A1 | 1/2015 | Wolcott et al. |
| 2015/0222358 | A1 | 8/2015 | Totten et al. |
| 2017/0302254 | A1 * | 10/2017 | McNamara ............. H04L 27/01 |
| 2017/0353750 | A1 | 12/2017 | Gotwals et al. |
| 2019/0229981 | A1 | 7/2019 | Chappel et al. |

OTHER PUBLICATIONS

Official Action for Canada Patent Application No. 3,060,291, dated Dec. 3, 2020 3 pages.

Official Action for Canada Patent Application No. 3,060,291, dated Sep. 16, 2021 4 pages.

Official Action for U.S. Appl. No. 16/664,604, dated Jul. 27, 2020 6 pages Restriction Requirement.

Official Action for U.S. Appl. No. 16/664,604, dated Oct. 22, 2020 12 pages.

Official Action for U.S. Appl. No. 16/664,604, dated Feb. 10, 2021 14 pages.

Notice of Allowance for U.S. Appl. No. 16/664,604, dated Jun. 24, 2021 9 pages.

Notice of Allowance for Canada Patent Application No. 3,060,291, dated Aug. 24, 2022 (Attorney's Ref. No. 3997-88-CA) 1 page.

Official Action for Canada Patent Application No. 3,184,557, dated May 6, 2024 4 pages.

* cited by examiner

SYSTEMS AND METHODS FOR CONTROLLING HOSPITALITY DISTRIBUTION NETWORKS

CROSS-REFERENCE TO RELATED APPLICATIONS

This application is a continuation application of U.S. patent application Ser. No. 16/664,604, filed Oct. 25, 2019, which claims the benefit of U.S. Provisional Patent Application Ser. No. 62/751,310, filed Oct. 26, 2018, the entire disclosures of each of which are incorporated herein by reference for all that the teach and for all purposes.

FIELD

Example embodiments are generally directed to systems and methods for controlling a distribution network that distributes content and/or data, for example, in a hospitality environment.

BACKGROUND

Increasingly, connectivity for content and/or data services, is delivered to users over digital networks. In a hospitality or healthcare environment, it is desirable to provide high quality connectivity services to all active users. Because signal levels in such an environment are subject to variations due to degraded components, added or removed components, etc., signal levels may be monitored along the transmission path and adjusted to account for these variations. Thus, it is desired to employ distribution systems and/or methods that allow for convenient monitoring and adjustment of signals traveling the network.

SUMMARY

According to at least one example embodiment, systems and methods provide for signal monitoring and adjustment of the same for signal distribution networks (SDNs). In more detail, example embodiments provide a connected amp host (CAH) that provides centralized control for amplifiers located at desired positions within the SDN. In addition, each amplifier has its own processing and two-way communication capabilities that assist with signal monitoring and adjustment. Thus, example embodiments include amplification elements capable of measuring signal strength/quality and capable of receiving and transmitting data signals, control signals, reporting signals, etc. The amplification elements are connected to the CAH, which allows the CAH to utilize signal measurements and targets to automate signal adjustment at each amplifier across the SDN.

According to at least one example embodiment, the amplifier elements may include a quadrature amplitude modulation (QAM) tuner and a microprocessor or the like to provide measurements on signal level, signal quality, frequency agility, etc., to provide receiving/transmitting operations for measured data and commands to adjust amplifier settings.

Additional features and advantages of embodiments of the present disclosure will become more readily apparent from the following description, particularly when taken together with the company drawings.

DETAILED DESCRIPTION

Figure 1:
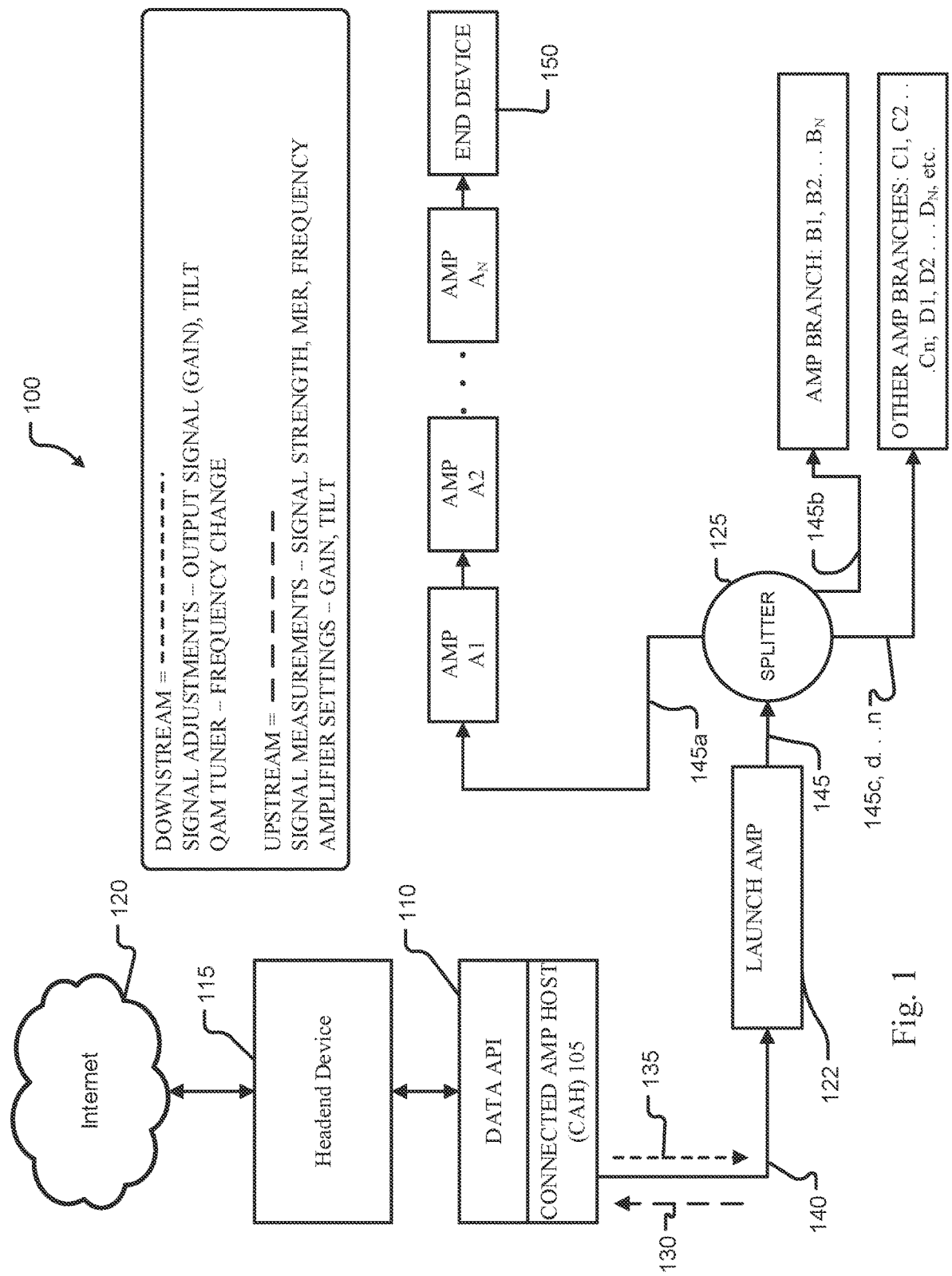
FIG. 1 is a block diagram depicting components of a system in accordance with example embodiments.

FIG. 1 is a block diagram depicting components of a system 100 in accordance with example embodiments. In more detail, FIG. 1 shows that the system 100 includes a connected amp host (CAH) or host device 105 in communication with a data application program interface (API) 110 that allows for graphical user interaction with the CAH 105. The CAH 105 includes hardware and/or software for controlling the overall operation of the amplifiers A1, A2 . . . $A_N$, B1, B2 . . . $B_N$, etc. (e.g., microprocessors, ASICs, etc.). The system 100 further includes a headend device 115 coupled to the data API 110 and the CAH 105 and that communicates with the internet 120 to transmit content and/or data services. As also shown, the system 100 includes a launch amplifier 122 for receiving a signal (e.g., a content signal including audio and/or video or other test signal) 140 from the CAH 105, and for outputting an amplified signal 145 (e.g., an amplified content signal including audio and/or video) to the splitter 125. The splitter 125 is coupled to one or more branches (A, B, C, D, etc.) of amplifiers (A1, A2, B1, B2, etc.). The splitter 125 splits the signal 145 received from the launch amplifier 122 into multiple signals 145*a*, 145*b*, 145*c* . . . 145*n*, where a number of split signals is equal to the number of amplifier branches, and sends the split signals to the various branches of amplifiers A, B, C. Aside from inherent signal loss characteristics of the splitter 125, the split signals 145*a*, 145*b*, etc. are substantial replica signals in gain, frequency, modulated data, etc. of the signal output from launch amplifier 122.

As also shown in FIG. 1, each branch A, B, C, etc. of amplifiers is capable of upstream communication 130 and downstream 135 communication with the CAH 105 (details of branch A are illustrated for the sake of completeness). A last amplifier in each branch may be connected to an end device 150, such as a test device or test terminal. In the example of FIG. 1, the end device 150 is an MATV test device, for example, a signal meter, Set Top Box (STB) or display device in a hotel room. The end device 150 may be capable of measuring one or more signal characteristics (or signal parameters) of the content signal 145*a* (or, alternatively, a test signal), discussed in more detail below. In one example, the end device 150 or in-room device (or test device) does not communicate signal characteristic measurements, so signal measurements may be taken by a technician at each amplifier and the technician may enter settings (gain, attenuation, equalization, preemphasis, etc.) at each respective amplifier (e.g., using the external device 245) or on a global level if configured through the CAH 105 in order to achieve a desired signal level output for each amplifier A1, A2 . . . $A_N$, etc.

As shown, upstream communication 130 may include each amplifier sending measured signal characteristics of the signal 145a to the CAH 105. Measured signal characteristics may include signal strength (in dB), modulation error ratio (MER), signal frequency, bit rate (in Mbps), etc. These measurements can be taken at the end device 150 input, the end device 150 output, an amplifier input, an amplifier output, or any combination of these, as desired. Upstream communication 130 may also include each amplifier sending its associated settings to the CAH 105. Amplifier settings may include gain, tilt, slope, attenuation, equalization, pre-emphasis, etc. The CAH 105 may perform operations to adjust the signals at one or more of the amplifiers in order to improve system-wide signal strength and/or quality at desired test devices. Operations of the system 100 are discussed in more detail below.

Downstream communication 135 may include signals from the CAH 105 that pass through the amplifiers to communicate adjustments for the amplifiers (e.g., in gain, tilt, slope, etc.) and/or tuning instructions for the QAM tuner. The downstream communication 135 may begin at the CAH 105 and proceed through each amplifier in each branch of amplifiers.

Here, it should be understood that the upstream communication 130 and the downstream 135 communication described above may be performed in accordance with any known wireless or wired communications protocol (see, for example, communication methods described in U.S. Pat. Nos. 5,641,319 and 6,343,315, the entire contents of each of which are herein incorporated by reference). Here, it should be understood that upstream communication 130 and downstream communication 135 may occur over a same means of communication as the signal 140, for example, a same cable such as CATV cable, Ethernet cable, etc.

Although not explicitly shown, it should be further understood that more end devices 150 may be connected to the end of the amplifier branch shown in FIG. 1 or to points between amplifiers in the branch as desired.

Figure 2:
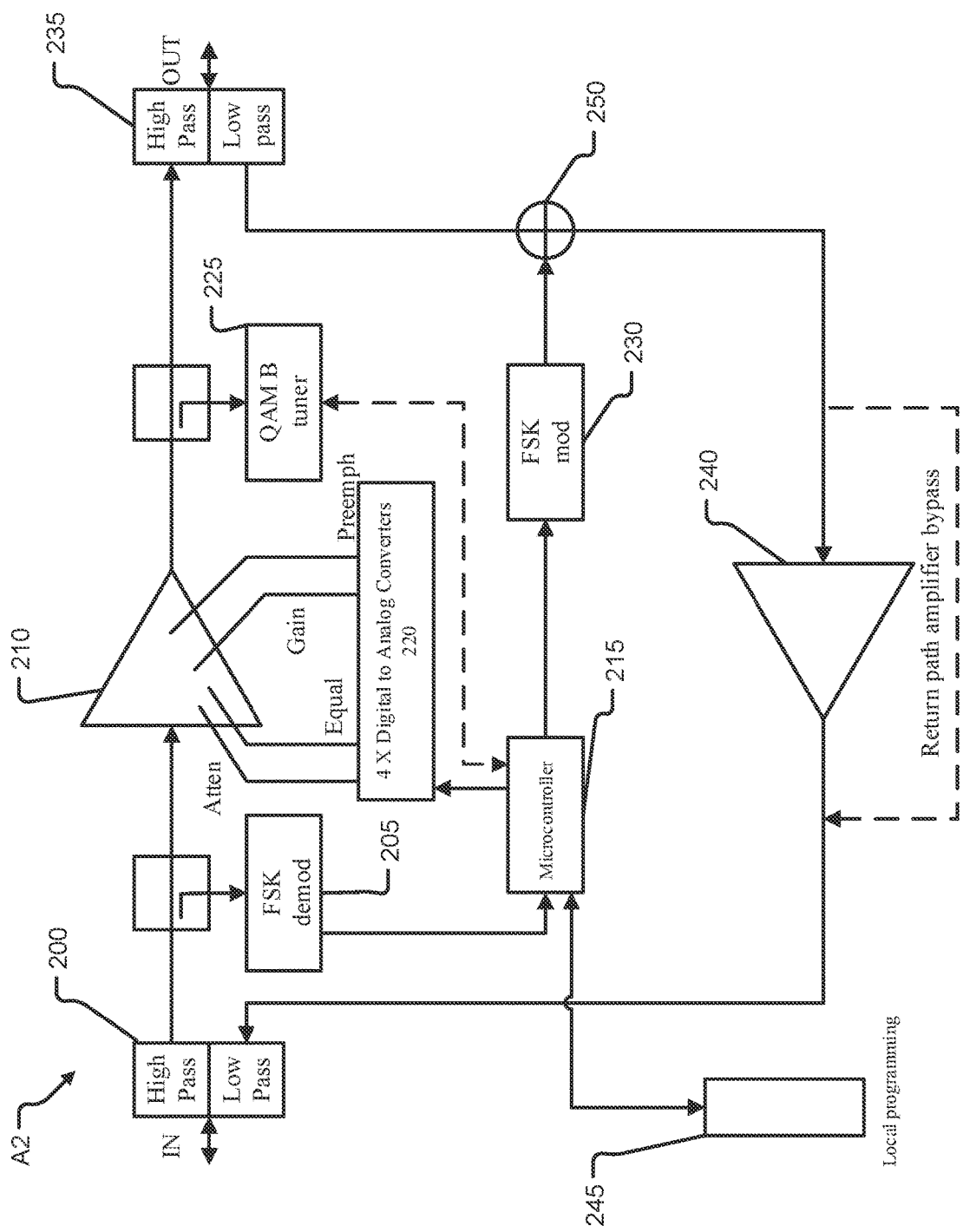
FIG. 2 is an example structure of one of the amplifiers in FIG. 1 in accordance with example embodiments.

FIG. 2 illustrates an example structure of an amplifier in FIG. 1 (e.g., amplifier A2) in accordance with example embodiments. As shown in FIG. 2, the amplifier A2 includes an input filter circuit 200 and an output filter circuit 235. The input and output filter circuits 200/235 may each include a high pass filter and a low pass filter. As shown, signals for downstream communication 135 (e.g., toward end device 150) received at input IN and output at output OUT may be passed through respective high pass filters, and signals for upstream communication 130 (e.g., toward the CAH 105) may be passed through respective low pass filters. Upstream communication 130 and downstream communication 135 may occur at different frequencies. For example, downstream signaling 135 (including signal 140) occurs at frequencies from about 49 MHz to about 1002 MHz, and upstream signaling 130 occurs at frequencies from about 5 MHz to about 36 MHz.

FIG. 2 also shows an amplification element 210 having an input coupled to the input filter circuit 200. The amplification element 210 may be an analog amplifier that alters a received signal according to one or more other inputs that indicate amplifier settings, such as attenuation, equalization, gain, preemphasis, etc. An output of the of the amplification element 210 is coupled to a tuner 225. According to at least one example embodiment, the tuner 225 is a quadrature amplitude modulation (QAM) tuner that receives a signal from an output of the amplification element 210, and outputs a signal to the microcontroller (or controller) 215. The tuner 225 may measure signal level (e.g., in dB), signal quality (e.g., SNR), or other signal metrics/characteristics as part of the embedded tuner functions. The tuner may also provide frequency agile tuning capabilities to allow it to perform measurements on multiple frequencies.

FIG. 2 also shows a demodulator 205 coupled to the input filter circuit 200, and a microcontroller 215 that is coupled to an output of the demodulator 205. According to at least one example embodiment, upstream signaling 130 and downstream 135 signaling utilizes a frequency-shift keying (FSK) modulation scheme which the demodulator 205 can receive and/or transmit. The demodulator 205 may demodulate a signal or message received from the input filter circuit 200 and send the demodulated signal and its associated data to the microcontroller 215 for processing. The demodulated signal may be analyzed by the microcontroller 215 to extract settings for the amplification element 210 such as gain, attenuation, equalization, preemphasis, etc. to the microcontroller 215.

The microcontroller 215 is coupled to a modulator 230 and converters 220. The microcontroller 215 interprets the received demodulated signal (e.g., extracts settings for the amplification element 210) and outputs corresponding signals to the converters 220 to adjust settings of the amplification element 210. For example, the microcontroller 215 extracts information embedded in the demodulated signal and calculates a difference between expected/desired points and measured or current points for one or more settings of the amplification elements 210 (attenuation, equalization, gain, preemphasis, slope, tilt, etc.), and then sends signals to adjust the one or more settings to their expected/desired points. In other words, all traffic originating from the CAH 105 may be received by each demodulator 205 and sent to a respective microcontroller 215. Each microcontroller 215 then determines whether the received message (e.g., a header of the message) contains an identifier (e.g., a unique identifier) associated with a respective amplifier A1, A2 . . . . $A_N$, etc. (see FIG. 4, which refers to the example of FIG. 2). If so, the microcontroller 215 processes the remainder of the message to extract the desired points of the one or more settings and adjusts the one or more settings accordingly. If not, the microprocessor 215 ignores the received message and continues to monitor received messages for the unique identifier associated with the respective amplifier A2.

The modulator 230 may be an FSK modulator, and the converters 220 may be digital to analog converters for supplying signals to the amplification element 210 to control attenuation, equalization, gain, preemphasis, etc. The modulator 230 may modulate a signal output from the microcontroller 215 according to an FSK modulation scheme. The modulated signal may represent one or more the aforementioned amplifier settings and/or signal characteristic measurements set or determined by the microcontroller 215. The amplifier A2 includes an adder 250 for (combining and passing through) the modulated signal to another signal received (e.g., another modulated signal from another amplifier) from the low pass filter of the output filter circuit 235. These operations may occur in accordance with known standards/protocols, such as the data over cable service interface specification (DOCSIS). This allows signals for two or more disparate purposes to co-exist within the same signal distribution path. The resultant signal is sent to the low pass filter of the input filter circuit 200 through another amplification element 240. Here, it should be appreciated that the resultant signal represents part of the upstream communication 130 to the CAH 105. For example, the resultant signal may represent one or more the aforementioned amplifier settings and/or signal measurements of amplifier A2 and/or settings/measurements of other downstream amplifiers and/or and signal measurements from end device 150. According to at least one example embodiment, the resultant signal bypasses the amplification element 240, for example, when no amplification is required to meet distribution system signal requirements (e.g., the signal is strong enough without further amplification).

The microcontroller 215 is connectable to an external device 245. The external device 245 may be used for on-site monitoring of the signal(s) at amplifier A2 and/or to provide local programming of the microcontroller 205. For example, the external device 245 communicates with the microcontroller 215 over a wired and/or wireless interface to monitor signals at the amplifier A2 and/or to control settings of the amplification element 210, such as attenuation, gain, equalization, preemphasis, etc. The amplifier structure for amplifier A2 shown in FIG. 2 may be the same for each amplifier in each branch of amplifiers.

Figure 3:
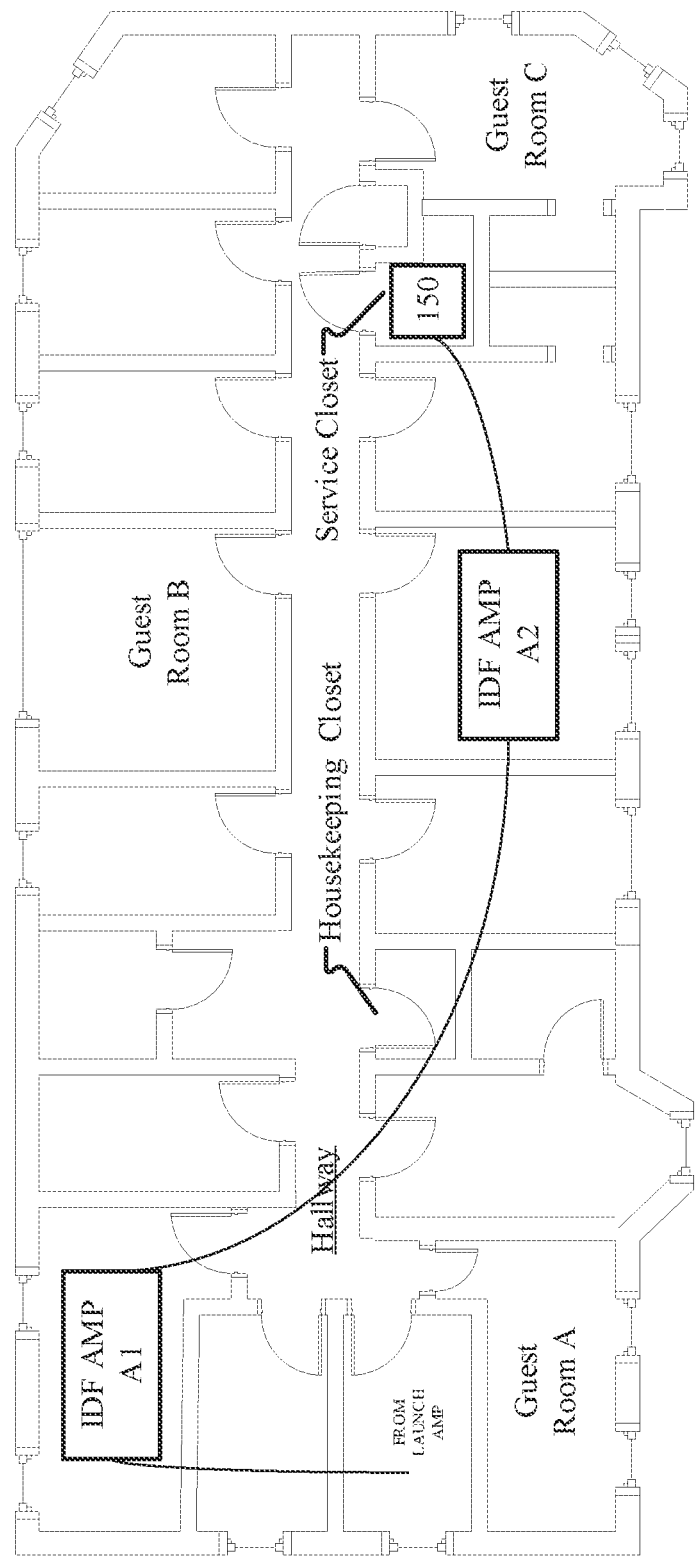
FIG. 3 illustrates an environment for the of FIG. 1 in accordance with example embodiments.

FIG. 3 illustrates an environment for the system 100. Here, the environment may be a hospitality location (hotel, motel, inn, etc.) or healthcare facility (acute care hospital, clinic, etc.) that includes a plurality of guest or patient rooms and other service related rooms. As shown in FIG. 3, amplifier A1 receives a signal from the launch amplifier 122. Amplifier A1 is connected to amplifier A2 which is in turn connected to the end device 150. As noted above, the end device 150 may be a signal meter, Set Top Box (STB) or other located in one of the guest or patient rooms and/or located in one of the service rooms.

Figure 4:
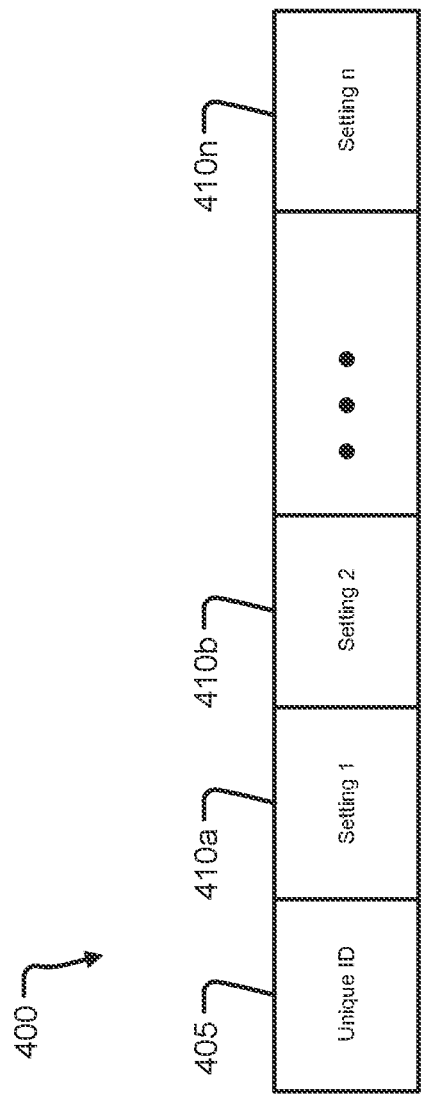
FIG. 4 illustrates a message sent in downstream communication of the system in FIG. 1 in accordance with example embodiments.

FIG. 4 illustrates a message 400 sent in the downstream communication 135 of the system 100 in FIG. 1.

As shown in FIG. 4, the message 400 includes fields 405 and 410a-410n. Field 405 may include a unique identifier (ID) of an associated amplifier A1, A2 . . . $A_N$, etc. The unique identifier may be any identifier that is unique to the associated amplifier so that the associated amplifier is readily identifiable by the microcontroller 215 as being the amplifier for which the message is intended. In at least one example embodiment, the unique identifier is a unique (e.g., random) combination of bits. With reference to the example of amplifier A2 in FIG. 2, when the signal including the message 400 is demodulated by the demodulator 205, the microcontroller 215 may determine that the unique ID is associated with amplifier A2, meaning that a remainder of the message is intended for the amplifier A2. In this case, the microcontroller 215 may continue analyzing the received demodulated signal to extract settings 1, 2 . . . n from fields 410a to 410n for the amplification element 210. As noted above, each field 410a-410n may correspond to gain, tilt, slope, attenuation, equalization, preemphasis, etc. of the amplification element 210. Although not explicitly shown, each field 410a to 410n may include information to identify which setting is in that particular field, and to identify an actual value of the setting. In accordance with example embodiments, the microcontroller 215 extracts the settings from the message and applies the settings to the amplification element 210.

Figure 5:
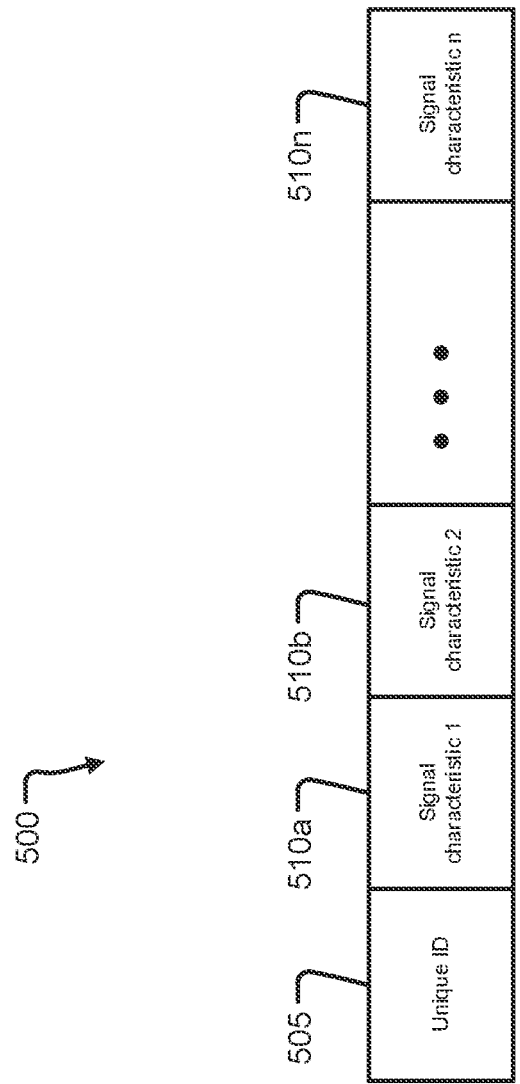
FIG. 5 illustrates a message sent in upstream communication of the system in FIG. 1 in accordance with example embodiments.

FIG. 5 illustrates a message 500 sent in the upstream communication 130 of the system 100 in FIG. 1.

As shown in FIG. 5, the message 500 includes fields 505 and 510a-510n. The message 500 is useful for transmitting measured signal characteristics from the branch of amplifiers A1, A2, $A_N$ to CAH 105. The signal characteristics may be the characteristics of a content signal (e.g., an audio and/or video signal 145) provided from the headend 115 to the end device 150. Field 505 may include a unique identifier (ID) of an associated amplifier A1, A2 . . . $A_N$. The unique identifier may be any identifier that is unique to the associated amplifier so that the associated amplifier is readily identifiable as being the amplifier from which the message originate. In at least one example embodiment, the unique identifier is a unique (e.g., random) combination of bits. With reference to the example of amplifier A2 in FIG. 2, when the signal including the message 500 is modulated by the modulator 230 with measured signal characteristics from tuner 225, the microcontroller 215 may add the unique ID associated with amplifier A2 to the message so that the CAH 105 can determine that a remainder of the message is from the amplifier A2. In this case, the CAH 105 may continue analyzing the received signal to extract signal characteristics 1, 2 . . . n from fields 510a to 510n, and store the extracted signal characteristics as being from amplifier A2. In accordance with at least one example embodiment, the extracted signal characteristics from each amplifier in the branch are compared to desired signal characteristics for the content signal 145 at each amplifier in the branch. The CAH 105 may use the comparison to determine adjusted settings for amplifier A2, which are then sent via downstream communication 135 in accordance with the message 400 above. As noted above, each field 510a-510n may correspond to signal strength (in dB), modulation error ratio (MER), signal frequency, bit rate (in Mbps), etc. of the content signal 145 (or other test signal). Although not explicitly shown, each field 510a to 510n may include information to identify which signal characteristic is in that particular field, and to identify an actual value of the signal characteristic.

Figure 6:
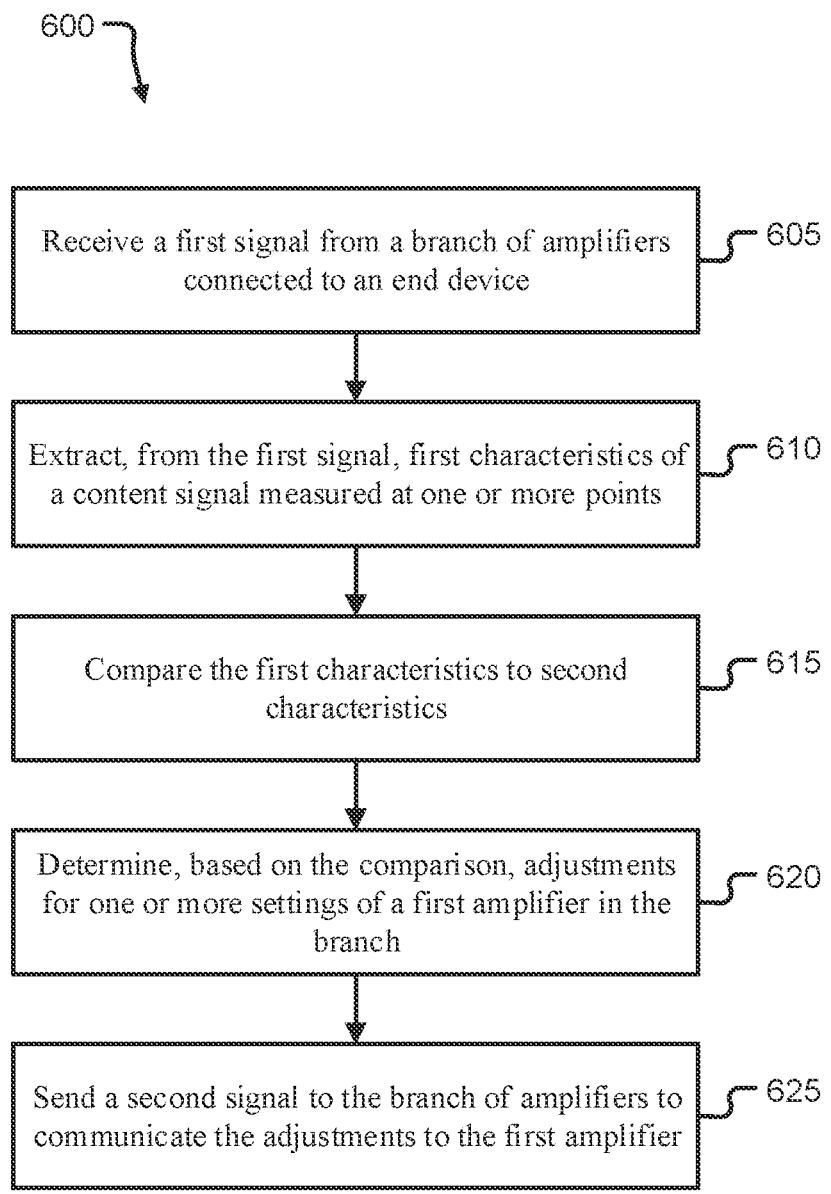
FIG. 6 illustrates an example method for the system in FIG. 1 in accordance with example embodiments.

FIG. 6 illustrates an example method 600 for the system 100 in FIG. 1. For example, the operations of FIG. 6 are carried out by the CAH 105. The operations of FIG. 6 will be discussed with reference to FIGS. 1-5, and with reference to the amplifier A2 in FIG. 2.

In operation 605, the method includes receiving a first signal from a branch of amplifiers A1, A2 . . . $A_N$ connected to an end device 150. The first signal may be a signal in the upstream communication 130 carrying information regarding characteristics of content signal 145a.

In operation 610, the method includes extracting, from the first signal, first characteristics 1, 2 . . . n of the content signal 145a measured at one or more points in the branch of amplifiers A1, A2, $A_N$. The one or more points may include at least one of a point between two amplifiers in the branch and a point between a last amplifier in the branch and the end device 150. In this example, the first characteristics may be measured at an input and/or an output of amplifier A2. The characteristics may include one or more of signal strength (in dB), modulation error ratio (MER), signal frequency, bit rate (in Mbps), etc., as measured by the tuner 225 or other suitable instrument at the amplifier A2 (e.g., the external device 245). The CAH 105 may extract the first characteristics from the first signal by demodulating the received modulated signal, and interpreting the demodulated signal. In at least one example embodiment, the one or more points includes at least one of a point between two amplifiers in the branch and a point between a last amplifier in the branch and the end device 150.

In operation 615, the method includes comparing the first characteristics of the content signal to second characteristics, where the second characteristics are desired (or expected) for the content signal at the one or more points. In this example, the second characteristics may be stored at and/or input to the CAH 105 as signal characteristics that are expected or desired for the content signal at the input and/or the output of the amplifier A2. These second characteristics may be static and/or variable and be based on design preferences and/or empirical evidence.

In operation 620, the method includes determining, based on the comparison in operation 615, adjustments for one or more settings of a first amplifier A2 of the amplifiers in the branch. For example, if the measured signal strength (or first signal characteristic) at the input and/or output of amplifier A2 is not within a desired threshold amount of the expected or desired signal strength stored or input at the CAH 105, then the CAH 105 may determine to alter settings of the amplifier A2 that decrease or increase the signal strength to be within the threshold amount of the expected or desired signal strength.

In operation 625, the method includes sending a second signal to the branch of amplifiers to communicate the adjustments for the one or more settings determined in operation 620 to the first amplifier A2. The second signal may be sent in accordance with the downstream communication 135 described above. For example, the CAH 105 modulates the second signal with the adjustments for the one or more settings and with a unique identifier associated with the first amplifier A2. As noted above, the amplifier A2 may demodulate the second signal to determine that the second signal contains the unique identifier, and apply, in response to determining that the second signal contains the unique identifier, the adjustments to the one or more settings of the amplification element 210. The method may return to operation 605 to determine whether the updated settings have brought the actual signal characteristics within the threshold amount, and if not, to continue to adjust the settings.

Here, it should be appreciated that the operations of FIG. 6 may be carried out for one or more of the other amplifiers in a same branch as amplifier A2 and/or one or more amplifiers in one or more other branches of FIG. 1.

In addition, it should be appreciated that FIG. 6 describes operations in which the CAH 105 determines adjustments to amplifier settings, and sends a signal to communicate those adjustments. However, example embodiments are not limited thereto, and each amplifier may be capable of making its own settings adjustments via the microcontroller 215 using measurements from the tuner 225. For example, the microcontroller 215 may be preprogrammed or programmed by the external device 145 to include certain thresholds for signal characteristics measurable by the tuner 225. If the feedback from the tuner 225 indicates that one or more of the measured signal characteristics is not within a threshold amount of an expected or desired amount, then the microcontroller 215 may adjust the settings of the amplification element 210 accordingly.

Figure 7:
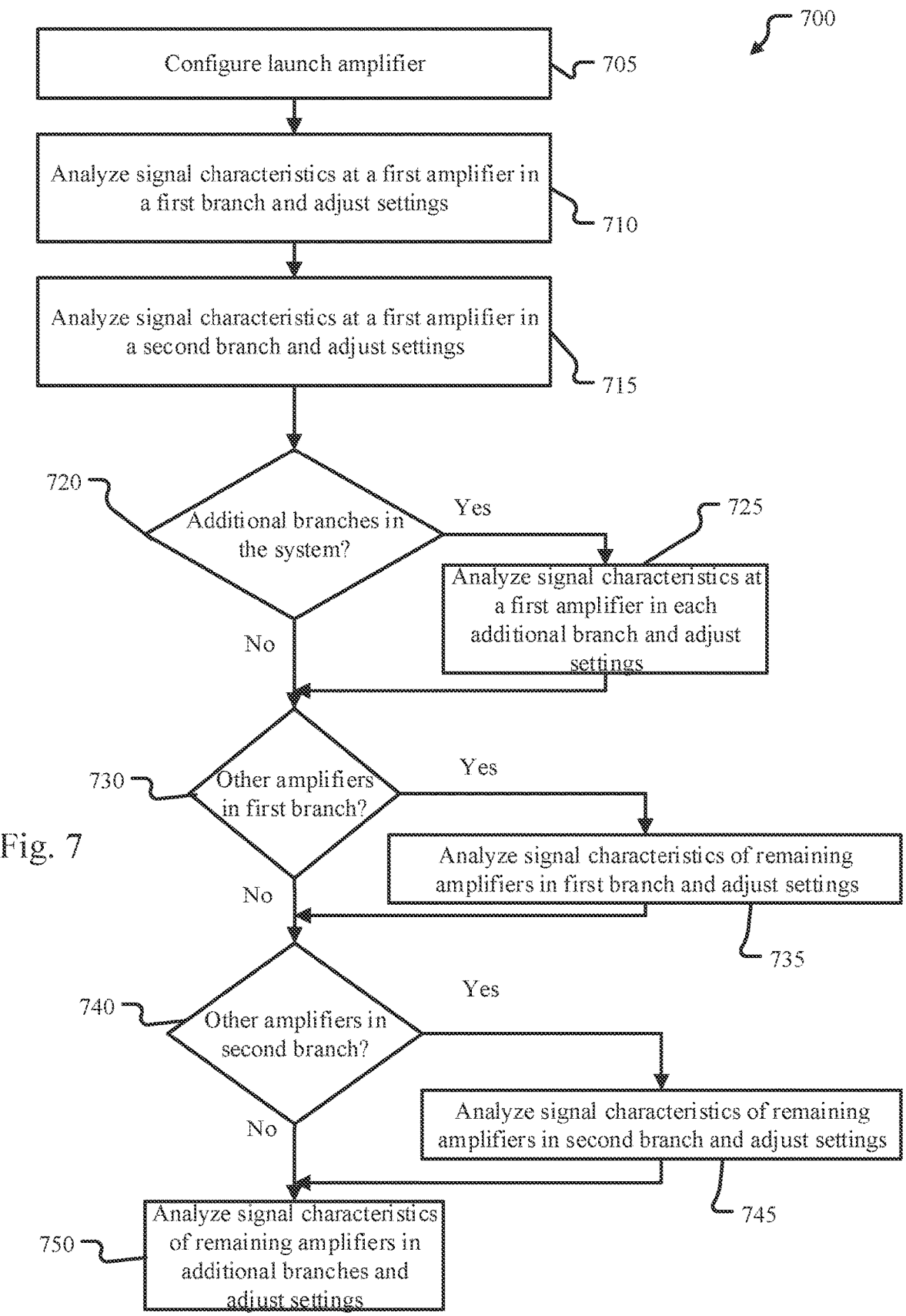
FIG. 7 illustrates an example method for the system in FIG. 1 in accordance with example embodiments.

FIG. 7 illustrates an example method 700 for the system 100. The operations of FIG. 7 may be carried out by the CAH 105, for example, and relate to adjusting amplifiers in all amplifier branches within the system 100. FIG. 7 will be described with reference to FIGS. 1-6.

In operation 705, the method includes configuring the launch amplifier 122. For example, the CAH 105 configures the launch amplifier 122 to meet desired signal characteristics and validate signal quality against a set of rules or thresholds (e.g., signal level, MER, SNR, etc.).

In operation 710, the method includes analyzing signal characteristics at a first amplifier in a first branch and adjusting the amplifier's settings accordingly. For example, the CAH 105 considers signal characteristics at the input and/or output at amplifier A1, and based on these readings the CAH 105 aligns amplifier A1 (e.g., by adjusting settings of the amplifier A1) and makes any desired changes to the settings of the launch amplifier 122 to optimize signal quality globally. If the upstream communication 130 received by the CAH 105 from amplifier A1 indicates that a signal level at the output of A1 should be adjusted (i.e., the signal level is above or below a target value), then the CAH 105 sends downstream communication 135 to amplifier A1 to adjust its settings accordingly. If in-room devices 150 are connected to the output of this amplifier A1, data may also be gathered/sourced from in-room devices 150 to validate proper signal level and quality.

In operation 715, the method includes analyzing signal characteristics at a first amplifier in a second branch and adjusting settings. For example, the CAH 105 considers signal characteristics at the input and/or the output at amplifier B1. Based on these readings, the CAH 105 will align amplifier B1 and make any desired changes to the settings of the launch amplifier 122 or amplifier A1 to optimize signal quality globally. This process will be repeated for all branches of the amplifiers. For example, in operation 720, the method determines whether there are additional amplifier branches in the system 100, and if so, the method proceeds to operation 725 to analyze signal characteristics at each first amplifier in each additional amplifier branch and adjusts settings of each first amplifier accordingly.

Once each first cascade amplifier (A1, B1, C1 . . . ) is balanced in operation 725 or if there are not more additional branches in operation 720, the method may proceed to operation 730 and balance the rest of the amplifiers in the network in a linear order, as outlined below.

For example, in operation 730, the method determines whether there are other amplifiers in the first branch of amplifiers. If so, the method proceeds to operation 735 to analyze signal characteristics at each remaining amplifier in the first branch and to adjusts settings accordingly. For example, balancing the remaining amplifiers in the network may include the CAH 105 considering signal characteristics at the input and/or the output at amplifier A2. Based on these readings, the CAH 105 will align amplifier A2 and make any desired changes to the settings of amplifier A1. If in-room devices 150 are connected to the output of this amplifier A2, data may also be gathered/sourced from in-room devices to validate proper signal level and quality. If the changes exceed desired specifications of the amplifiers, a notification will be sent to the technician (e.g., through an interface of the CAH 105) to review the distribution. Then, the CAH 105 considers signal characteristics at the input of an amplifier A3. Based on these readings, the CAH 105 will align amplifier A3 and make any desired changes to amplifier A2. If in-room devices 150 are connected to the output of this amplifier A3, data may also be gathered/sourced from in-room devices to validate proper signal level and quality. If changes exceed specifications of the amplifiers, a notification will be sent to the technician (e.g., through an interface of the CAH 105) to review the distribution. This pattern continues for all subsequent cascade amplifiers in the system 100.

For example, in operation 740, the method determines whether there are additional amplifiers in the second branch of amplifiers. If so, the method proceeds to operation 745 and analyzes signal characteristics of remaining amplifiers in the second branch of amplifiers and adjusts settings accordingly. Once all amplifiers in the second branch have been adjusted in operation 745 or if there are no additional amplifiers to adjust in operation 740, the method proceeds to operation 750.

In operation 750, the method includes analyzing signal characteristics of remaining amplifiers in each additional branch (e.g., C, D, etc.) in an amplifier-by-amplifier and branch-by-branch fashion in the same manner as that discussed above with respect to branches A and B.

Once all amplifiers have been adjusted, the CAH 105 may log the signal characteristics of each channel on the system 100 at each measurable point and routinely monitor the system 100 for variance. To monitor the system 100, the CAH 105 may receive signal characteristics from one or more of the amplifiers and/or the end device 150 at regular intervals (e.g., once per six hours or other desired time period) or upon request. If the CAH 105 detects behavior of system signaling metrics over time that deviate from expected norms or specifications, the system 100 generates a notification or alert. In addition, the system 100 may take steps to automatically correct any deviations in the same manner as described above.

Here, it should be appreciated that the analysis of signal characteristics and adjustment of amplifier settings may be carried out in accordance with the description of FIGS. 1-6.

In general, it should be understood that amplifier settings can be adjusted to achieve desired signal characteristics or properties received by the end device 150 and/or to achieve desired system performance. The desired signal characteristics or properties and desired system performance may be design parameters set based on empirical evidence and/or user preference. Furthermore, example embodiments may employ RF balancing algorithms, a user interface that allows remote access/monitoring for the amplifiers, and automated control algorithms (e.g., using a proportional-integral-derivative (PID) controller) to maintain system targets.

Here, it should be appreciated that the above described operations may be programmed to occur at regular time intervals (e.g., once per day, once per week, etc.). Alternatively, these operations occur on demand as desired (e.g., by a technician).

As indicated in the foregoing description, in order to monitor and control the settings of each amplifier individually, the amplifiers may be assigned unique identifiers in accordance with FIGS. 4 and 5 so that the CAH 105 can address selected ones of the amplifiers. For example, each unique identifier 405/505 may include a site identifier associated with a particular site (e.g., hotel location), a branch identifier to identify which branch A, B, or C etc. includes the amplifier, and/or an amplifier identifier to identify a position of the amplifier in its branch. The identifiers may consist of letters, number, symbols, text strings, etc. Thus, the CAH 105 can request measurements and settings of a particular one of the amplifiers, and also send adjustments to a particular one of the amplifiers.

Example embodiments may include one or more user interface devices executing mobile application and/or web browsers to allow for adjusting the amplifier settings, viewing monitoring data, and generating alerts when one of the amplifiers is operating outside of defined limits, etc.

In view of the above, it should be appreciated that example embodiments provide the ability to centrally monitor and control amplifiers in a distribution network, which increases efficiency of setting up and maintaining the network.

Accordingly, example embodiments have been described with some degree of particularity directed to the exemplary embodiments of the inventive concepts. It should be appreciated though that modifications or changes may be made to the exemplary embodiments without departing from the inventive concepts contained herein.

At least one example embodiment is directed to a system including a host device to provide a content signal, an end device to receive the content signal, and a branch of amplifiers connected between the host device and the end device to carry the content signal from the host device to the end device. The host device may receive a first signal from the branch of amplifiers connected to the end device, and extract, from the first signal, first characteristics of the content signal measured at one or more points in the branch of amplifiers. The host device may compare the first characteristics of the content signal to second characteristics, where the second characteristics are desired for the content signal at the one or more points. The host device may determine, based on the comparison, adjustments for one or more settings of a first amplifier of the amplifiers, and send a second signal to the branch of amplifiers to communicate the adjustments for the one or more settings to the first amplifier.

According to at least one example embodiment, the system further includes a launch amplifier coupled between the host device and the branch of amplifiers and that outputs the content signal from the host device to the branch of amplifiers.

According to at least one example embodiment, the system further includes additional branches of amplifiers, and a splitter that splits the content signal into a plurality of content signals for the additional branches of amplifiers.

According to at least one example embodiment, the first characteristics and the second characteristics include one or more of signal strength, signal frequency, signal quality, bit rate, and modulation error ratio of the content signal.

According to at least one example embodiment, the one or more settings include at least one of gain, equalization, attenuation, and preemphasis.

According to at least one example embodiment, the first amplifier includes an input filter circuit that receives and filters the second signal, a first amplification element coupled to the input filter circuit, a demodulator coupled between the first amplification element and the input filter circuit and that demodulates the second signal to output a demodulated signal, and a controller that extracts the adjustments for the one or more settings from the demodulated signal, and applies the extracted adjustments for the one or more settings to the first amplification element.

At least one example embodiment is directed to a method that includes receiving a first signal from a branch of amplifiers connected to an end device, and extracting, from the first signal, first characteristics of a content signal measured at one or more points in the branch. The method includes comparing the first characteristics of the content signal to second characteristics, the second characteristics being desired for the content signal at the one or more points. The method includes determining, based on the comparison, adjustments for one or more settings of a first amplifier of the amplifiers, and sending a second signal to the branch of amplifiers to communicate the adjustments for the one or more settings to the first amplifier.

According to at least one example embodiment, the method further includes modulating the second signal with the adjustments for the one or more settings and with a unique identifier associated with the first amplifier. The method further includes demodulating the second signal to determine that the second signal contains the unique identifier, and applying, in response to determining that the second signal contains the unique identifier, the adjustments to the one or more settings of the first amplifier.

According to at least one example embodiment, the first signal is modulated with the first characteristics.

According to at least one example embodiment, the one or more points includes at least one of a point between two amplifiers in the branch and a point between a last amplifier in the branch and the end device.

At least one example embodiment is directed to an amplifier including an input filter circuit that receives and filters an input signal, a first amplification element coupled to the input filter circuit, a demodulator that demodulates the filtered input signal to output a demodulated signal, and a controller that extracts one or more settings for the first amplification element from the demodulated signal, and applies the extracted one or more settings to the first amplification element.

According to at least one example embodiment, the amplifier further includes a tuner that receives a first output signal of the first amplification element, measures at least one characteristic of the first output signal, and sends the measured at least one characteristic to the controller.

According to at least one example embodiment, the controller generates a second output signal that represents the measured at least one characteristic.

According to at least one example embodiment, the amplifier further includes a modulator that modulates the second output signal.

According to at least one example embodiment, the amplifier further includes an adder that adds the modulated second output signal to another modulated output signal from a neighboring amplifier to output an added signal, and sends the added signal to the input filter circuit.

According to at least one example embodiment, the input filter circuit includes a first high pass filter and a first low pass filter.

According to at least one example embodiment, the input signal is directed through the first high pass filter, and the added signal is directed through the first low pass filter.

According to at least one example embodiment, the another modulated output signal is directed through a second low pass filter before being added to the modulated output signal.

According to at least one example embodiment, the amplifier further includes a second amplification element coupled between the input filter circuit and the adder and that amplifies the added signal.

According to at least one example embodiment, the one or more settings include gain, equalization, attenuation, and preemphasis.

The phrases "at least one", "one or more", "or", and "and/or" are open-ended expressions that are both conjunctive and disjunctive in operation. For example, each of the expressions "at least one of A, B and C", "at least one of A, B, or C", "one or more of A, B, and C", "one or more of A, B, or C", "A, B, and/or C", and "A, B, or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The terms "determine", "calculate" and "compute," and variations thereof, as used herein, are used interchangeably and include any type of methodology, process, mathematical operation or technique.

The term "means" as used herein shall be given its broadest possible interpretation in accordance with 35 U.S.C., Section(s) 112(f) and/or 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

As will be appreciated, other aspects, embodiments, and/or configurations of the disclosure are possible utilizing, alone or in combination, one or more of the features set forth above or described in detail below. Also, while the disclosure is presented in terms of exemplary embodiments, it should be appreciated that individual aspects of the disclosure can be separately claimed.

The invention claimed is:

1. A system comprising:
   an amplifier, comprising:
   an input filter circuit that receives and filters an input signal;
   a first amplification element coupled to the input filter circuit;
   a demodulator that demodulates the filtered input signal to output a demodulated signal; and
   a controller that extracts one or more settings for the first amplification element from the demodulated signal, and applies the extracted one or more settings to the first amplification element.

2. The system of claim 1, further comprising:
   a tuner that receives a first output signal of the first amplification element, measures at least one characteristic of the first output signal, and sends the measured at least one characteristic to the controller.

3. The system of claim 2, wherein the controller generates a second output signal that represents the measured at least one characteristic.

4. The system of claim 3, further comprising:
   a modulator that modulates the second output signal.

5. The system of claim 4, further comprising:
   an adder that adds the modulated second output signal to another modulated output signal from a neighboring amplifier to output an added signal, and sends the added signal to the input filter circuit.

6. The system of claim 5, wherein the input filter circuit includes a first high pass filter and a first low pass filter.

7. The system of claim 6, wherein the input signal is directed through the first high pass filter, and wherein the added signal is directed through the first low pass filter.

8. The system of claim 7, wherein the another modulated output signal is directed through a second low pass filter before being added to the modulated output signal.

9. The system of claim 5, further comprising:
   a second amplification element coupled between the input filter circuit and the adder and that amplifies the added signal.

10. The system of claim 1, further comprising:
    a host device; and
    an end device.

11. A system, comprising:
    a host device to provide a content signal;
    an end device to receive the content signal; and
    a branch of amplifiers connected between the host device and the end device to carry the content signal from the host device to the end device, the branch of amplifiers including a first amplifier with a controller configured to:
    receive a demodulated signal comprising a message;
    determine whether a header of the message comprises a unique identifier of the first amplifier;
    process the message when the header of the message comprises the unique identifier of the first amplifier by extracting adjustments for one or more settings of the first amplifier from the message and applying the extracted adjustments for the one or more settings to the first amplifier; and ignore the message when the header of the message does not comprise the unique identifier of the first amplifier.

12. The system of claim 11, further comprising:
a launch amplifier coupled between the host device and the branch of amplifiers and that outputs the content signal from the host device to the branch of amplifiers.

13. The system of claim 12, further comprising:
additional branches of amplifiers; and
a splitter that splits the content signal into a plurality of content signals for the additional branches of amplifiers.

14. The system of claim 11, wherein the one or more settings are based on one or more of signal strength, signal frequency, signal quality, bit rate, or modulation error ratio of the content signal as measured at the host device.

15. The system of claim 14, wherein the one or more settings include at least one of gain, equalization, attenuation, or preemphasis.

16. The system of claim 11, wherein the first amplifier includes:
an input filter circuit;
a first amplification element coupled to the input filter circuit; and
a demodulator coupled between the first amplification element and the input filter circuit and that outputs the demodulated signal, wherein the controller applies the extracted adjustments for the one or more settings to the first amplification element.

17. A method, comprising:
receiving, by a controller of an amplifier, a demodulated signal comprising a message;
determining, by the controller, whether a header of the message comprises a unique identifier of the amplifier;
processing, by the controller, the message when the header of the message comprises the unique identifier of the amplifier by extracting adjustments for one or more settings from the message and applying the extracted adjustments for the one or more settings to the amplifier; and
ignoring, by the controller, the message when the header of the message does not comprise the unique identifier of the amplifier.

18. The method of claim 17, further comprising:
modulating a first signal with the message; and
demodulating the first signal to form the demodulated signal.

19. The method of claim 17, wherein the one or more settings are based on one or more of signal strength, signal frequency, signal quality, bit rate, or modulation error ratio of a content signal as measured at a host device.

20. The method of claim 19, wherein the one or more settings include at least one of gain, equalization, attenuation, or preemphasis.

* * * * *